Figure 1:
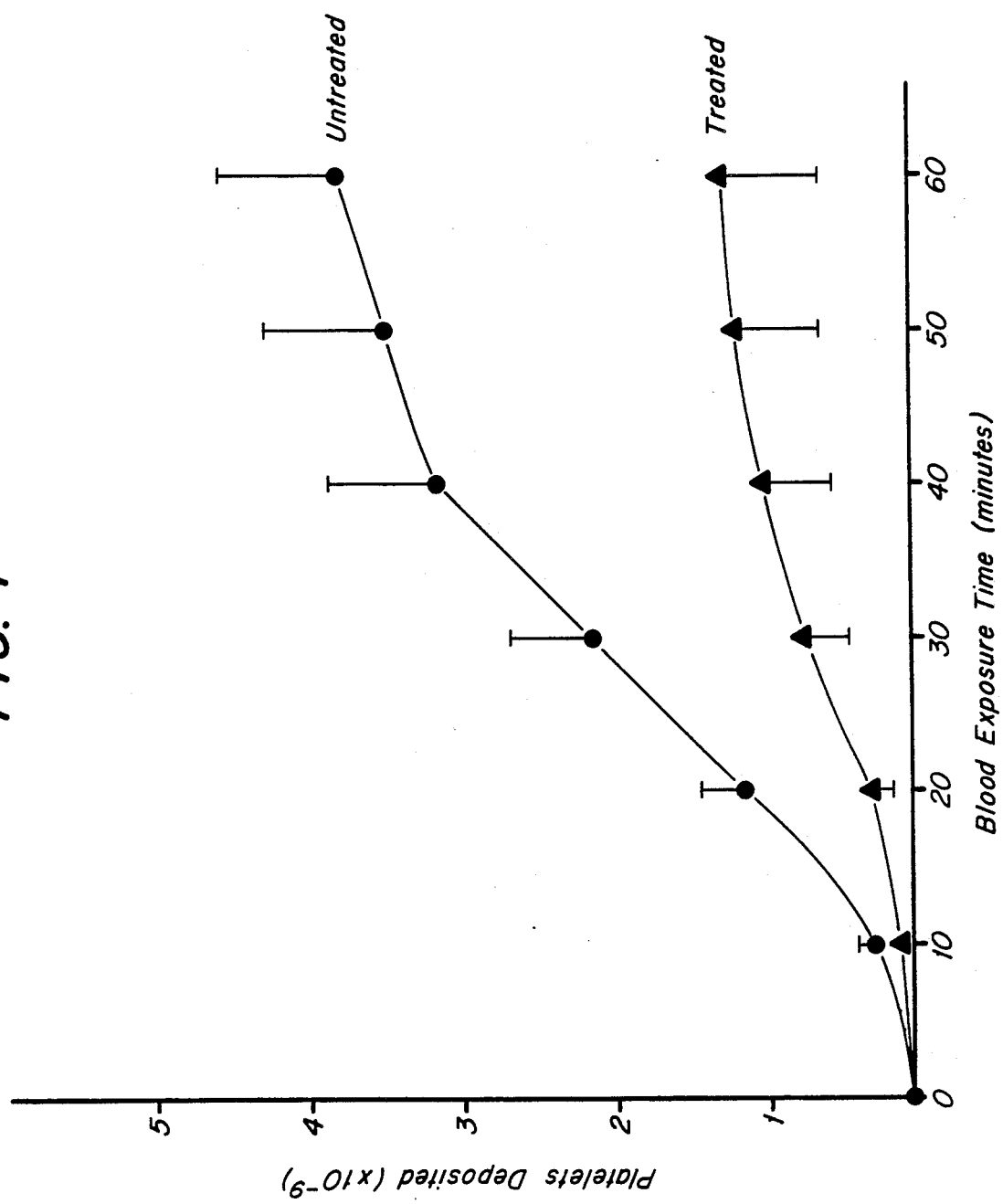

United States Patent [19]

Yasuda

[11] Patent Number: 4,994,298
[45] Date of Patent: Feb. 19, 1991

[54] METHOD OF MAKING A BIOCOMPATIBLE PROSTHESIS

[75] Inventor: Hirotsugu K. Yasuda, Newburg, Mo.

[73] Assignee: Biogold Inc., Wilmington, Del.

[21] Appl. No.: 512,543

[22] Filed: Apr. 18, 1990

Related U.S. Application Data

[63] Continuation of Ser. No. 203,116, Jun. 7, 1988, abandoned.

[51] Int. Cl.$^5$ ............................................. B05D 3/06
[52] U.S. Cl. ........................................ 427/41; 427/39; 427/38; 427/2; 623/1; 623/12
[58] Field of Search ............... 427/39, 38, 41, 2; 623/12, 16, 1; 118/730, 731

[56] References Cited

U.S. PATENT DOCUMENTS

| | | | |
|---|---|---|---|
| 3,839,743 | 10/1974 | Schwarcz | 623/11 |
| 4,164,794 | 8/1979 | Spector et al. | 623/16 |
| 4,188,426 | 2/1980 | Auerbach | 427/40 |
| 4,444,805 | 4/1984 | Corbett et al. | 427/41 |
| 4,636,435 | 1/1987 | Yanagihara et al. | 427/41 |
| 4,655,771 | 4/1987 | Wallsten | 623/1 |
| 4,656,083 | 4/1987 | Hoffman et al. | 428/265 |
| 4,673,588 | 6/1987 | Bringmann et al. | 427/41 |
| 4,690,097 | 9/1987 | Fukuta et al. | 118/723 |
| 4,718,907 | 1/1988 | Karwoski et al. | 427/2 |
| 4,776,337 | 10/1988 | Palmaz | 623/1 |

FOREIGN PATENT DOCUMENTS

| 57-12032 | 1/1982 | Japan |
| 58-208326 | 12/1983 | Japan |
| 2189150A | 10/1987 | United Kingdom |

Primary Examiner—Stanley Silverman
Assistant Examiner—Roy V. King
Attorney, Agent, or Firm—Burns, Doane, Swecker & Mathis

[57] ABSTRACT

A method of making a biocompatible hollow artifact with perforated walls made from a substrate of electroconductive material whose surface is exposed to a biological environment, such as living animal tissue or blood, to impart to said material biocompatibility at the site of exposure, comprising:

subjecting said exposed surface of the substrate to exposure to a plasma gas discharge in a plasma zone containing a plasma polymerizable monomeric gas to form a thin flexible coating on said substrate, said exposure being performed for a sufficient period of time and under relative movement between said plasma zone and said substrate, the volume of said plasma zone being capable of complete immersion of the substrate and being of such a magnitude in relation to the volume of the substrate as to enable the substrate to travel in or through the plasma zone under plasma polymerization without disturbing the plasma generation.

16 Claims, 2 Drawing Sheets

METHOD OF MAKING A BIOCOMPATIBLE PROSTHESIS

This application is a continuation, of application Ser. No. 203,116, filed June 7, 1988, now abandoned.

The present invention relates to a method of making a biocompatible hollow artifact with perforated walls made from a substrate of electro-conductive material, such as a metal. The surface of said substrate is intended for exposure to living animal tissue or blood.

BACKGROUND OF THE INVENTION

Artifacts or devices which are intended for use in a living animal body usually are made of materials having limited biocompatibility, such as non-thrombogenicity and compatibility vis-à-vis living tissue or blood. In the instant disclosure the term "animal" refers in particular to mammals including man. Such artifacts are therefore generally coated with surface coatings for improving the biocompatibility, such coating being made without affecting other important properties of the artifact. In recent years such coating of implantable artifacts has been provided by so called plasma polymerization. Such technique has been used mainly when coating artifacts made of polymeric materials. Plasma polymerization generally is based on introducing a gas comprising one or more polymerizable organic monomers into a vacuum zone, wherein the material to be coated is placed. The polymerizable monomers are then subjected to an electric discharge for initiating polymerization reactions by the generation of ions of free radicals reacting with each other and also with the substrate when made of an organic material perform a deposit on the substrate. The polymerizable monomers are often constituted by fluorinated hydrocarbons, such as tetrafluoroethylene.

Although plasma polymerization for modifying biomaterials has been used as early as in the late 1960's relatively little work has been done until recent years, but presently the number of publications and patents is rapidly increasing and plasma polymerization has become increasingly interesting for improving the surface properties of implantable devices or artifacts.

As examples of close prior art there may be mentioned U.S. Pat. Nos. 3,839,743, 4,188,426 and 4,656,083, each relating to technique for improving the biocompatibility of implantable devices or prostheses. However, in regard to this prior art it is evident that the plasma polymerization to provide for biocompatibility is applied solely to non-metallic substrates, whereby adherence of the polymer coating obtained to the underlying substrate is greatly facilitated due to the fact that covalent bonds can be formed between substrate and coating in the plasma polymerization process.

The present invention deals exclusively with substrates made of electro-conductive materials, such as metallic materials, and furthermore, substrates which are hollow and have perforated walls. In particular, the invention is directed to tubular substrates of metallic materials. When trying to solve the problem of coating such electro-conductive substrates using plasma polymerization it will be immediately clear that due to the fact that the substrate acts as a Fareday's cage the plasma polymerization fails to function properly in that inside such cage no generation of plasma will occur and thus no deposition of polymer.

The main object of the present invention is to provide a new method of manufacturing biocompatible hollow artifacts with perforated walls made from a substrate of electro-conductive material by depositing a coating onto said substrate which results in improved biocompatibility at the site of implantation of such prosthesis into a living animal body.

Another object of the invention is to enable manufacture of tubular artifacts with perforated walls made from a substrate of electro-conductive material using plasma gas discharge in a plasma zone containing a plasma polymerizable monomeric gas to form a biocompatible thin flexible coating on said substrate.

Yet another object of the invention is to provide prostheses, the substrates of which are coated with a carbonaceous coating of improved biocompatibility, such as non-thrombogenicity and tissue or blood compatibility.

Still another object of the invention is to provide techniques for coating expandible tubular stents, such as self-expanding ones, with a thin flexible, strongly adhering coating of excellent biocompatibility.

SUMMARY OF THE INVENTION

While the invention is applicable to any biocompatible hollow artifacts with perforated walls made from a substrate of electro-conductive material the invention will be illustrated in the following mainly with reference to metallic tubular and perforated substrates, such as expandible tubular stents. It must be noted, however, that the invention is not limited solely to such metallic artifacts.

In regard to plasma coating of metallic tubular and perforated substrates by plasma polymerization it has been discovered in accordance with the present invention that the Fareday's cage problem can be solved by a new method involving the following steps.

A substrate of metallic material whose surface is exposed to living animal tissue or blood is subjected to a plasma gas discharge in a plasma zone containing a plasma polymerizable monomeric gas. Such exposure is performed under relative movement between the plasma zone and the substrate. In order to obtain an operable process the volume of the plasma zone used must be of such a magnitude in relation to the volume of the substrate as to enable the substrate to move in or through the plasma zone under plasma polymerization without disturbing the plasma generation. It has been found that if the plasma zone volume is of the same order of magnitude as the substrate volume then the plasma generation will automatically cease due to the Faraday's cage phenomenon.

In this disclosure the substrate volume is the volume contained within an imaginary space surface circumscribing the substrate of metallic material.

It is preferred that said plasma zone volume is at least about ten times larger than said substrate volume and particularly at least about one hundred times larger than said volume.

From a practical point of view it is preferred to arrange for relative movement between the plasma zone and the substrate by moving the substrate in relation to a plasma zone of fixed location. The substrate can be allowed to travel repeatedly into, through and out of said plasma zone, the number of passages being sufficient to provide by deposition a coating of the desired thickness on the substrate.

Alternatively, the substrate can be moved within said plasma zone for a desired period of time. To ensure even deposition of polymer the substrate may be subjected to both translational and rotational movement in relation to the plasma zone. It is particularly preferred to impart to the substrate movement along a circular path.

Although the present invention is applicable to the manufacture of any biocompatible tubular and perforated prosthesis based on a substrate of metallic material, it was particularly unexpected that it was possible to effectively coat by plasma polymerization so called stents of the self-expanding type. Clearly, the coating is subjected to considerable stress and strain in connection with contraction and expansion of such tubular stent and it was therefore surprising that the adherence of the coating was of such a strong nature as to resist manipulation of the stent.

Although the present invention is in no way limited thereto it is particularly suited for application on expandable prostheses as disclosed in U.S. Pat. No. 4,655,771. The invention is also of particular interest in relation to further developments of such prostheses as disclosed in published U.K. Pat. application No. 2,189,150. (The disclosures of these specifications are incorporated herein by reference thereto).

In accordance with said U.S. patent the self-expanding tubular stent is composed of a plurality of individual rigid but flexible and elastic thread elements each of which extends in helix configuration along and around the centerline of said stent as a common axis, said stent being provided with a first number of thread elements having a common direction of winding and being axially displaced relative to each other, and with a second number of thread elements also axially displaced relative to each other but having an opposite direction of winding thus crossing said first number of thread elements. The crossing thread elements are preferably arranged in a braid-like configuration so as to impart stability to the stent. It is clear from said patent specifications that the diameter of the stent is variable under axial movement of the ends of the stent relative to each other.

It is preferred to use in the method of this invention monomers selected from fluorinated hydrocarbons and hydrocarbons having 1 to 6 carbon atoms. It is particularly preferred to use fluorinated hydrocarbons and hydrocarbons having 1, 2 or 3 carbon atoms. As examples of such monomers there may be mentioned tetrafluoroethylene, hexafluoroethane, perfluoropropylene, methane, ethane and such monomers can be used in different combinations with or without hydrogen.

Mixtures of tetrafluoroethylene and methane can be used in roughly equal proportions, and such mixtures may be diluted using hydrogen. Alternatively, solely a pure hydrocarbon may be used as a monomeric gas. It is also possible to use mixtures of methane and hydrogen. When using a halogenated hydrocarbon in combination with hydrogen the plasma discharge will result in reactions whereby a corresponding hydrogen halogenide, such as hydrofluoric acid, escapes in gaseous form. In the plasma polymerization process it is generally preferred that the monomeric gas is free from oxygen-containing constituents. Due to the presence of un-paired electrones, i.e. free-radicals, in the deposited coating some oxygen from the environment may be found on the surface of the coating. but will not constitute any problem with regard to biocompatibility of the coating.

In this disclosure the term "biocompatible" has the meaning biologically non-interfering rather than any meaning in the direction of providing any specific bioactivity. Thus, the principal object of providing a surface coating in accord with this invention is to create a biologically inert surface of a non-interfering character.

The conditions for the plasma polymerization to deposit the coating on a substrate are not of a critical nature but it is preferred to use high plasma energy density expressed as Joules per kilogram monomers and hydrogen, such value preferably being above 1 GJ/kg. The minimum value varies with the type of monomeric gas used, and as examples there may be mentioned that when using methane as a monomer the value is about 8 GJ/kg, whereas when using fluorinated hydrocarbons together with hydrogen the lower value of about 1 can be used.

The reactor used for the plasma polymerization is quite generally of a conventional character but shall be designed to allow for sufficient residence time of reactor species in the plasma state, i.e. provision of sufficient kinetic path length before deposition occurs, and this can be achieved by combinations of plasma volume, system pressure and plasma energy density.

The invention will now be further described below by non-limiting examples.

In the following examples the metallic stents modified by plasma polymerization are exposed to flowing blood using a baboon arteriovenous shunt system described by Hanson et al., Arteriosclerosis 5:595, 1985. The medicinal implants were placed inside a 10 cm length of rigid-walled Teflon tubing (Small Parts Inc. Miami, Florida, USA). In all cases these Teflon tubings containing stents or grafts are placed between the arterial and venous silicone rubber tubing segments comprising a chronic femoral arteriovenous (A-V) shunt in baboons as described by Hanson et al. loc.cit. The thrombogenicity in regard to platelet adhesion of both untreated and plasma polymer modified artifacts or deplants is determined by dynamaic scintillation camera imaging of the accumulation of autologous blood platelets labeled with Indium-111-oxine following exposure to flowing blood in the baboon A-V shunt system. The results are expressed as the total number of platelets deposited over one hour according to the method described by Hanson et al., loc.cit.

EXAMPLES

EXAMPLE 1

A stent of the type described in UK patent application No. 2,189,150 having a diameter of 3.5 mm, a length of 30 mm ($\phi$ of filament=0.08 mm, n=16) is placed on a substrate holding device constituted by an aluminum disc having a diameter of 300 mm and a thickness of 1 mm and having equally spaced four openings of the dimension 40 mm × 155 mm. The stent is fastened in the opening of the sample holding disc by means of small clips located at both ends of the opening. The sample holding disc is placed at equidistance from two electrodes used in a Plasma Polymerization Apparatus of the type LCVD--12-400A, Shimadzu Corporation, Kyoto, Japan. The two electrodes are assisted by magnetic enhancement providing the maximum parallel component with respect to the electric field of a magnetic field of approximately 600 Gauss and the distance between the two electrodes is approximately 120 mm.

The sample holding disc is rotated in such a manner that the stent will pass the center portion of plasma volume created by the two parallel electrodes at a rate of approximately 30 rpm. After evacuation of the reactor to approximately 1 mtorr methane gas is introduced into the reactor at a rate of 0.5 sccm, and plasma polymerization is initiated by applying 150 watts. Plasma polymerization is sustained till a stationary thickness monitor, located near the edge of the rotating substrate holding disc indicates that the accumulated thickness of deposition onto the sensor reaches approximately 100 nm, corresponding to approximately 30 nm on the rotating stent. The coating prepared by the process has a refractive index of about 1.9 and an estimated value $(F+H)/C$ of about 0.8.

In the biological testing five coated stents were used and compared to ten untreated control stents. At all time points over the 60 minute blood exposure period using the techniques described above platelet deposition onto the five treated stents is markedly reduced as compared to the number of platelets deposited onto the ten untreated control stents. For example, after 60 minutes exposure to flowing blood the untreated stents accumulated $3.8 \pm 0.8 \times 10^9$ platelets ($\pm 1$SEM) while the treated stents accumulated only $1.3 \pm 0.7 \times 10^9$ platelets, i.e. platelet deposition was reduced by 66% ($p<0.01$, unpaired Student t-test).

The results of the platelet deposition experiments are illustrated in FIG. 1 of the drawing, wherein deposited platelets are plotted against blood exposure time in minutes.

EXAMPLE 2

Example 1 is repeated but using stainless steel stents having a diameter of 6 mm and a length of 150 mm. After evacuation of the reactor to approximately 1 mtorr a mixture of methane and hydrogen in the ratio of one to one is introduced into the reactor at a rate of 0.5 sccm, and plasma polymerization is initiated by applying 150 watts. Plasma polymerization is sustained till a stationary thickness monitor indicates an accumulated thickness of deposition of approximately 100 nm, corresponding to about 30 nm deposition on the rotating stent. The atomic ratio $(F+H)/C$ is approximately 0.9.

Five stents coated as described above are tested for a 60 minute blood exposure period in baboons, and the platelet deposition was compared to the deposition on untreated control stents. After 60 minutes of blood exposure the untreated stents accumulated $3.8 \pm 0.8 \times 10^9$ platelets ($\pm 1$ SEM), while the coated stents accumulated only $1.3 \pm 0.6 \times 10^9$ platelets, i.e. platelet deposition is reduced by 66% ($p<0.01$, unpaired Student t-test).

Figure 2:
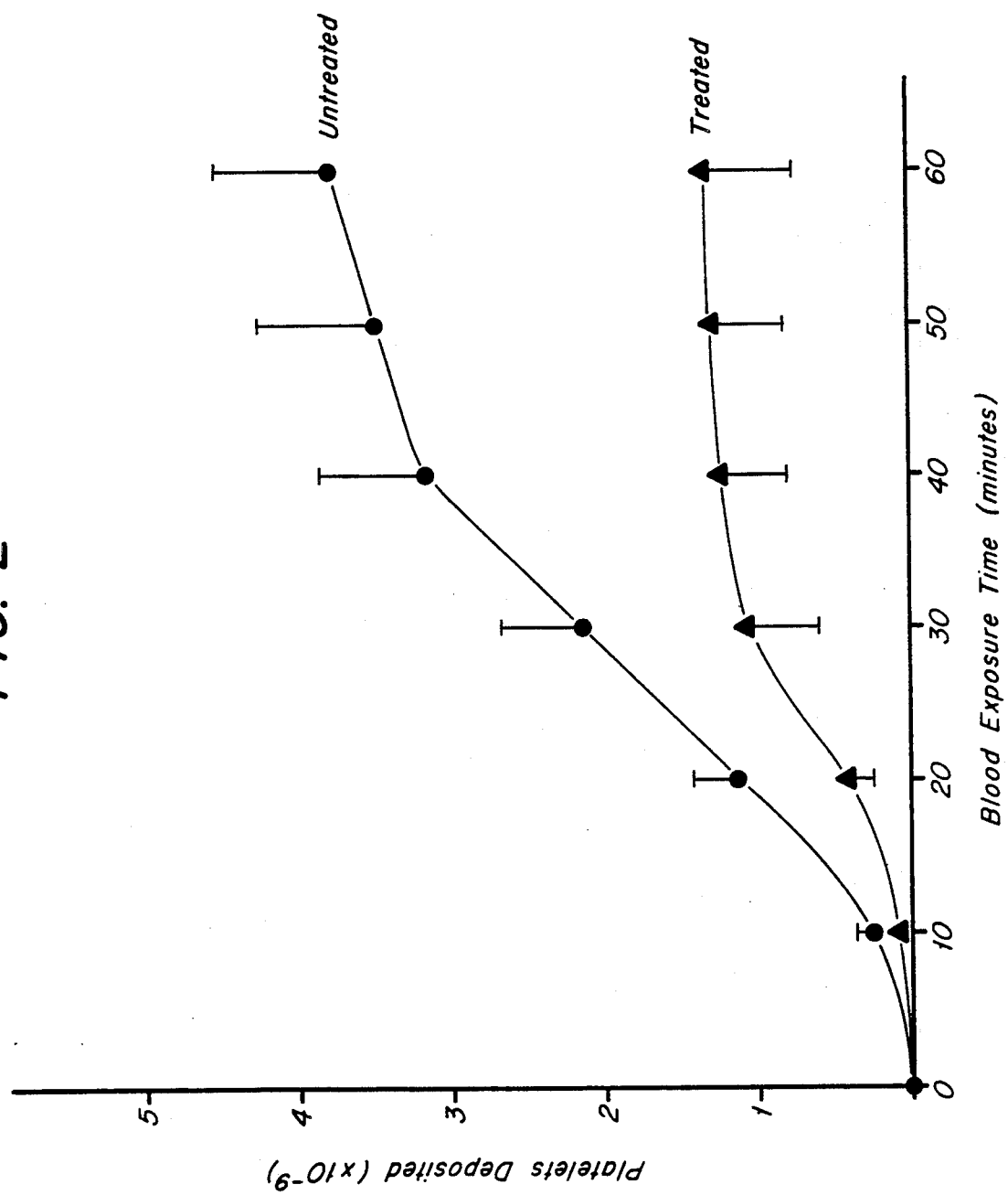

The experimental results are shown in appended FIG. 2, wherein deposited platelets are plotted against blood exposure time in minutes.

EXAMPLE 3

The same apparatus as used in Example 1 is used and stainless steel stents of the same type as in Example 2 are placed on the aluminum disc of the apparatus. However, the electrodes of the reactor are replaced by a hollow anode system designed as follows.

The hollow anode system consists of an aluminum cup, 100 mm × 100 mm and of 50 mm depth, the cup being connected to two aluminum plates, 100 mm × 50 mm, via dielectric materials (Macor, Corning Glass, Corning, NY, USA) in the plane of the opening side of the cup. One terminal of a radio frequency (rf) power supply is connected to the cup and another terminal is connected to the two plates. Monomeric gas is fed into the cup through an inlet, which is attached to the back side of the cup. The hollow anode system is placed parallel to the rotating disc maintaining a distance of approximately 30 mm.

After the reactor is evacuated to approximately 1 mtorr, a mixture of methane and tetrafluoroethylen in a ratio of one to one is introduced at a flow rate of 0.5 sccm, and plasma polymerization is initiated by applying 50 watts. The stent is coated uniformly after five minutes' operation. During this period the stent passes through plasma created in the space determined by the cup and the rotating plates, repeated passages being obtained at the rotating rate of approximately 30 rpm. A piece of silicone wafer is placed on the surface of the rotating disc to collect film sample for measurement of the refractive index by Elipsometry. The thin coating obtained has a refractive index of about 1.8 and the atomic ratio $(F+H)/C$ is approximately 0.9.

The biological properties of the coated stents are similar to those obtained with the stents treated according to Example 2.

EXAMPLE 4

The same procedure as described in Example 1 is used but the stent is mounted on the rotating plate by nylon clips in order to electrically isolate the stent from the rotating disc, which becomes cathode vis-à-vis the anode. With this electrically floating stent coating of plasma polymer is achieved with similar efficiency and the coating obtained has similar biological properties as that of Example 1.

I claim:

1. A method of making a biocompatible hollow artifact having perforated walls from a substrate of electro-conductive material which has a surface exposed to a biological environment including living animal tissue or blood, to impart to said material biocompatibility at the site of exposure, comprising:

subjecting said exposed surface of the substrate of said electro-conductive material to exposure to a plasma gas discharge in a plasma zone containing a plasma polymerizable monomeric gas to form a thin flexible coating on said substrate, said exposure being performed for a predetermined period of time and during relative movement between said plasma zone and said substrate, said substrate traveling in and out of the plasma zone under plasma polymerization without disturbing plasma generation.

2. A method according to claim 1, wherein the volume of said plasma zone is at least about ten (10) times larger than that of said substrate.

3. A method according to claim 1, wherein the substrate is moved in a circular path.

4. A method according to claim 1, where the substrate travels within said plasma zone for a predetermined period of time.

5. A method according to claim 1, wherein said substrate is subjected to both translational and rotational movement to ensure even deposition of polymer.

6. A method according to claim 1, wherein said substrate is an expandable tubular stent.

7. A method according to claim 6, wherein said stent is composed of a plurality of individual rigid but flexible and elastic thread elements each of which extends in helix configuration along and around the centerline of said stent as a common axis, said stent being provided with a first number of thread elements having a common direction of winding and being axially displaced relative to each other, and with a second number of thread elements also axially displaced relative to each other but having an opposite direction of winding thus crossing said first number of thread elements.

8. A method according to claim 7, wherein the crossing thread elements are arranged in a braid-like configuration so as to impart stability to the stent.

9. A method according to claim 1, wherein said monomeric gas contains monomers selected from hydrocarbons and halogenated hydrocarbons, optionally together with hydrogen, to deposit onto the substrate a thin and flexible carbonaceous layer.

10. A method according to claim 9, wherein said monomers are selected from fluorinated hydrocarbons and hydrocarbons having 1 to 6 carbon atoms.

11. A method according to claim 10, wherein said monomeric gas contains tetrafluoroethylene.

12. A method according to claim 2, where the substrate travels within said plasma zone for a predetermined period of time.

13. A method according to claim 3, wherein said substrate is subjected to both translational and rotational movement to ensure even deposition of polymer.

14. A method according to claim 4, wherein said substrate is subjected to both translational and rotational movement to ensure even deposition of polymer.

15. A method according to claim 12, wherein said substrate is subjected to both translational and rotational movement to ensure even deposition of polymer.

16. A method according to claim 7, wherein said monomeric gas contains monomers selected from hydrocarbons and halogenated hydrocarbons, optionally together with hydrogen, to deposit onto the substrate a thin and flexible carbonaceous layer.

* * * * *